United States Patent [19]

Singh et al.

[11] Patent Number: 5,384,107

[45] Date of Patent: Jan. 24, 1995

[54] IODINATED AROMATIC COMPOUNDS

[75] Inventors: Baldev Singh; Edward R. Bacon, both of East Greenbush, N.Y.; Carl R. Illig, Phoenixville, Pa.

[73] Assignee: Sterling Winthrop Inc., New York, N.Y.

[21] Appl. No.: 285,595

[22] Filed: Aug. 3, 1994

Related U.S. Application Data

[63] Continuation of Ser. No. 990,306, Dec. 14, 1992, abandoned.

[51] Int. Cl.[6] .............................................. A61K 49/04
[52] U.S. Cl. ........................................ 424/5; 560/47; 560/45; 560/37
[58] Field of Search .................. 560/47, 45, 37; 424/5

[56] References Cited

U.S. PATENT DOCUMENTS 3,772,376 11/1973 Ekstrand et al. ................... 260/518

FOREIGN PATENT DOCUMENTS 2111127 10/1971 Germany .

OTHER PUBLICATIONS

J. Med. Chem. 20(8), 1086–90 Brain et al., 1977.
Chemical Abstracts 76:24919 b; 1971 Search Report of Structures in 76: 24919b.

*Primary Examiner*—José G. Dees
*Assistant Examiner*—Samuel Barts
*Attorney, Agent, or Firm*—William J. Davis

[57] ABSTRACT

Compounds having the structure

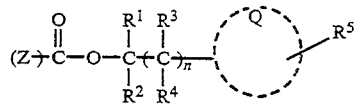

wherein $(Z)$-COO is the residue of an iodinated aromatic acid;

n is an integer from 0 to 6;

$R^1$ and $R^2$ are independently H, alkyl, fluoroalkyl, cycloalkyl, aryl, aralkyl, alkoxy or aryloxy;

$R^3$ and $R^4$ are independently H, alkyl, fluoroalkyl, cycloalkyl, aryl, aralkyl, alkoxy, aryloxy, halogen, hydroxy or acylamino;

Q represents the atoms necessary to complete a carbocyclic or heterocyclic unsaturated mono- or bicyclic aromatic ring; and $R^5$ is H, alkyl, cycloalkyl, aryl, aralkyl, alkoxy, aryloxy, halogen, hydroxy, amino, acylamino, alkoxyalkyl, fluoroalkyl, acetamidoalkyl, COO-alkyl, cyano, carboxamido, sulfonate, sulfonamido, ureido, or carbamyl are useful as contrast agents in x-ray imaging compositions and methods.

7 Claims, No Drawings

IODINATED AROMATIC COMPOUNDS

This is a continuation of copending application Ser. No. 07/990,306, filed Dec. 14, 1992, now abandoned.

FIELD OF INVENTION

This invention relates to iodinated aromatic compounds which are particularly useful as contrast agents for x-ray imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging*, 1990, MacMillan Publishing Company.

Various soluble and water insoluble iodinated amides and esters have been used as x-ray contrast agents. For example, U.S. Pat. No. 3,097,228 describes derivatives of 2,4,6-triiodobenzoyloxyalkanoic acids having the structure wherein $R^1$ is H or lower alkyl, $R^2$ is H or alkanoyl, $R^3$ is H or alkanoylamino, and $R^4$ is lower alkyl.

U.S. Pat. No. 3,144,479 describes iodinated benzoic acid esters having the formula wherein X is an iodine atom or an amino group and R is selected from H, alkyl, alkoxyalkyl, i.e., $-(CH_2)_m-O-R''$, wherein R'' is alkyl and m is 1 or 2, phenyl and a particular iodinated aromatic group.

However, these references do not disclose or suggest compounds featuring an aromatic group linked through an alkylene group to an ester group on an iodinated aromatic ring.

EP-A 498,482 describes nanoparticulate x-ray contrast compositions which have proven to be extremely useful in medical imaging. However, particulate contrast agents in certain in vivo applications can exhibit less than fully satisfactory enzymatic degradability, e.g., in lymph fluids, plasma or blood.

It would be desirable to provide compounds for use as x-ray contrast agents having improved enzymatic degradability and appropriate solubility profiles.

SUMMARY OF THE INVENTION

We have discovered and prepared novel iodinated aromatic compounds which are useful as x-ray contrast agents. The compounds feature an aromatic group linked through an alkylene group to an ester group on an iodinated aromatic ring.

More specifically, in accordance with this invention, there are provided compounds having the structure $$(Z)_{\overline{y}}C(=O)-O-C(R^1)(R^2)-[C(R^3)(R^4)]_n-Ar(Q)(R^5) \quad (I)$$

wherein (Z—COO is the residue of an iodinated aromatic acid;

n is an integer from 0 to 6;

$R^1$ and $R^2$ are independently H, alkyl, fluoroalkyl, cycloalkyl, aryl, aralkyl, alkoxy or aryloxy;

$R^3$ and $R^4$ are independently H, alkyl, fluoroalkyl, cycloalkyl, aryl, aralkyl, alkoxy, aryloxy, halogen, hydroxy or acylamino;

Q represents the atoms necessary to complete a carbocyclic or heterocyclic unsaturated mono- or bicyclic aromatic ring; and $R^5$ is H, alkyl, cycloalkyl, aryl, aralkyl, alkoxy, aryloxy, halogen, hydroxy, amino, acylamino, alkoxyalkyl, fluoroalkyl, acetamidoalkyl, COO-alkyl, cyano, carboxamido, sulfonate, sulfonamide, ureido, or carbamyl.

This invention further provides an x-ray contrast composition comprising the above-described compound and a method for medical x-ray diagnostic imaging which comprises administering to the body of a mammal a contrast effective amount of the above-described x-ray contrast composition.

It is an advantageous feature of this invention that novel compounds are provided which find particular utility as x-ray contrast agents.

It is another advantageous feature of this invention that compounds are provided having appropriate solubility profiles and improved enzymatic degradability.

DESCRIPTION OF PREFERRED EMBODIMENTS

In structural formula I above, (Z—COO is the residue of an iodinated acid. The iodinated aromatic acid can comprise one, two, three or more iodine atoms per molecule. Preferred species contain at least two, and more preferably, at least three iodine atoms per molecule. The iodinated compounds can contain substituents which do not deleteriously effect the contrast enhancing capability of the compound.

Illustrative examples of suitable aromatic acids include
diatrizoic acid,
metrizoic acid,
urokonic acid,
iothalamic acid,
trimesic acid,
ioxaglic acid (hexabrix),
ioxitalamic acid,
tetraiodoterephthalic acid,
iodipamide, and the like.

In preferred embodiments, (Z)—COO is the residue of a substituted triiodobenzoic acid such as an acyl, carbamyl, and/or acylamino substituted triiodobenzoic acid.

$R^1$ and $R^2$ independently represent H; linear or branched alkyl, preferably containing from 1 to 20, more preferably 1 to 8 carbon atoms such as methyl, ethyl, propyl, isopropyl, butyl, pentyl, hexyl and the like; fluoroalkyl, containing from 1 to (2m+1) fluorine atoms (where m=the number of carbon atoms in the alkyl group), the alkyl portion of which is as described above, such as trifluoromethyl; cycloalkyl, preferably containing from 3 to 8 carbon atoms such as cyclopropyl, cyclobutyl, cyclopentyl, and cyclohexyl; aryl, preferably containing from 6 to 10 carbon atoms, such as phenyl and naphthyl; aralkyl, preferably containing from 7 to 12 carbon atoms, such as benzyl; alkoxy, the alkyl portion of which contains from 1 to 20 carbon atoms as described above; or aryloxy, the aryl portion of which preferably contains from 6 to 10 carbon atoms as described above.

$R^3$ and $R^4$ independently represent a substituent as defined for $R^1$ above; halogen, such as chlorine, bromine or iodine; hydroxy; or acylamino, i.e., a

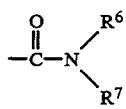

group wherein $R^6$ and $R^7$ are independently H, alkyl, cycloalkyl, aryl, aralkyl or alkoxy as defined for $R^1$ above, alkoxyalkyl, the alkyl and alkoxy portions of which are as defined for $R^1$ above, acetamidoalkyl, i.e.,

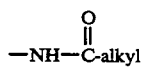

wherein alkyl is as defined for $R^1$ above, —COO—alkyl, the alkyl portion of which is as defined for $R^1$ above, cyano and the like, or $R^6$ and $R^7$, taken together with the nitrogen atom to which they are attached, represent a 4-7 membered saturated or unsaturated nitrogen containing ring such as piperidyl, piperizinyl, pyrrolidinyl, and the like. However, reactive substituents such as halogen, hydroxy, and acylamino are not preferred on the carbon atom adjacent to the carbocyclic or heterocyclic aromatic ring.

Q represents the atoms necessary to complete a carbocyclic or heterocyclic unsaturated aromatic radical. The aromatic radical can be monocyclic or bicyclic and preferably contains 5 to 12 ring atoms. The heterocyclic radical preferably contains one or more S, N or O atoms as the heteroatoms. Examples of preferred carbocyclic aromatic radicals include phenyl and naphthyl. Examples of preferred heterocyclic aromatic radicals include thienyl, furanyl, pyridyl, pyrrolyl, quinolyl, thiazolyl, imidazolyl, pyrimidyl, pyrazinyl, and like. In particularly preferred embodiments, Q represents the atoms necessary to complete a phenyl radical.

$R^5$ is one or more, preferably from one to three, and more preferably one, substituent selected from H, alkyl, cycloalkyl, aryl, aralkyl, alkoxy or aryloxy as defined for $R^1$ above; halogen, such as fluorine, chlorine, bromine and iodine; hydroxy; amino, i.e., a

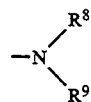

group wherein $R^8$ and $R^9$ are independently substituents as defined for $R^6$ and $R^7$ above; acylamino, the amino portion of which is as described above; alkoxyalkyl, the alkyl and alkoxy portions of which are as defined for $R^1$ above; fluoroalkyl, as defined for $R^1$ above; acetamidoalkyl, i.e.,

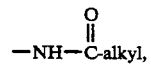

wherein alkyl is as defined for $R^1$ above; —COO—alkyl, the alkyl portion of which is as defined for $R^1$ above; cyano; carboxamido; sulfonate; sulfonamide; ureido; carbamyl and the like.

The alkyl, cycloalkyl, aryl, aralkyl and alkoxy groups in $R^1$–$R^5$ of structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine and iodine, acylamino, carboalkoxy, carbamyl and the like.

The compounds of this invention can be prepared by contacting the carboxylate of an iodinated aromatic acid with a functionalized derivative having the formula

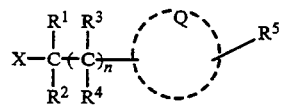

wherein X is a leaving group and Q and $R^1$–$R^5$ are as defined above. Suitable leaving groups include halogen, such as Br, I and Cl, sulfonyloxy, such as methanesulfonyloxy and toluenesulfonyloxy. The carboxylates of iodinated aromatic acids and functionalized derivatives useful as the starting materials in the preparation of the compounds of this invention are known compounds and/or can be prepared by techniques known in the art. For example, suitable functionalized derivatives include those derivatives as exemplified below. A general reaction scheme is as follows:

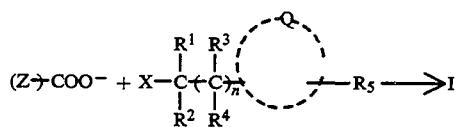

The reaction can take place at various temperatures ranging from between −78° C. and 100° C., preferably between −40° C. and 50° C., depending primarily upon the starting materials selected. For convenience, the reaction can take place at ambient temperature. However, heating can facilitate completion of the reaction.

For convenience, the reaction can take place at ambient pressure, however, higher and lower pressures are contemplated.

The reaction can take place in any suitable solvent. Suitable solvents include N,N-dimethylformamide.

The following are specific illustrative examples of preferred compounds of this invention that have been prepared:

4-(ethoxycarbonyl) phenyl 3,5-bis (acetylamino)-2,4,6-triiodobenzoate (WIN 67923), 4-(2-propoxycarbonyl)phenyl 3,5-bis (acetylamino) 2,4,6-triiodobenzoate (WIN 67956), 4-methoxyphenyl 3,5-bis (acetylamino) -2,4,6-triiodobenzoate (WIN 67754), 4-cyanophenyl 3,5-bis (acetylamino) -2,4,6-triiodobenzoate (WIN 67922), 3,4,5-trimethoxyphenyl 3,5-bis (acetylamino) -2,4,6-triiodobenzoate (WIN 69738), (3,5-diiodo-4-methoxy) phenyl 3,5-bis (acetylamino) 2,4,6-triiodobenzoate (WIN 69720), 4-methoxyphenyl 3-acetylamino-5-acetyl (methyl)-amino-2,4,6-triiodobenzoate (WIN 68887), benzyl 3,5-bis (acetylamino)-2,4,6-triiodobenzoate (Compound A), and benzyl N,N'-di-n-hexyl 3,5-bis (acetylamino) -2,4,6-triiodobenzoate (Compound B).

Preferred compounds of this invention conform to Structure I above, wherein $R^1$ and $R^2$=H, Q=phenyl and n=0 as set forth below.

| WIN | Z | $R^5$ |
|---|---|---|
| 67923 | ![structure with CH₃CONH, I, I, I, NHCOCH₃ on benzene ring] | $4\text{-}CO_2C_2H_5$ |
| 67956 | " | $4\text{-}CO_2CH(CH_3)_2$ |
| 67754 | " | $4\text{-}OCH_3$ |
| 67922 | " | $4\text{-}CN$ |
| 69738 | " | $3,4,5\text{-}(OCH_3)$ |
| 69720 | " | $2,6\text{-}(I); 4\text{-}OCH_3$ |
| A | " | H |
| 68887 | ![structure with CH₃COHN, I, I, I, NCOCH₃ with CH₃ on N] | $4\text{-}OCH_3$ |
| B | ![structure with CH₃CON(n-C₆H₁₃), I, I, I, NCOCH₃(n-C₆H₁₃)] | H |

When used as an x-ray contrast agent, the compound of this invention preferably comprises at least about 35%, more preferably 40% iodine by weight.

In preferred embodiments, the compounds of this invention can be formulated into particulate x-ray contrast compositions, preferably nanoparticulate x-ray contrast compositions, as described in commonly-owned EPO 498,482, the disclosure of which is hereby incorporated by reference in its entirety. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethylcellulose. Such additives, surface active agents, preservatives and the like can be incorporated into the compositions of the invention.

A method for diagnostic imaging for use in medical procedures in accordance with this invention comprises administering to the body of a mammal in need of an x-ray examination an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screensilver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1 Preparation of WIN 67754

To a stirred solution of sodium diatrizoate (25 g, 39 mmol) in 200 ml of N,N-demethylformamide (DMF) was added 4-methoxybenzyl chloride (5.8 ml, 42 mmol) over a 30 minute period. The resulting mixture was stirred overnight at ambient temperature. Additional 4-methoxybenzyl chloride (1 ml) was then added and the mixture was stirred for 24 hrs. The solvent was removed under reduced pressure leaving a white solid residue which was slurried in 300 ml of distilled water. The crude product was collected, washed with water and dried at 70°–75° C. to give a solid which was then digested with 400 ml of chloroform-isopropanol(1:1). Upon cooling, the solid was collected and dried under vacuum at 80°–85° C. to give the product (24.3 g, 85% yield) as a white granular solid, mp 244°–246° C.; CI-MS:MH+735. The $^1$H-NMR(300 MHz) spectral data was consistent with the desired product. Calculated for $C_{19}H_{17}I_3N_2O_5$; C 31.09, H 2.33, I 51.86, N 3.82; Found: C 31.05, H 2.23, I 51.84, N 3.84.

EXAMPLE 2 Preparation of WIN 67923

Preparation of Ethyl 4-bromomethylbenzoate

A mixture of ethyl 4-methylbenzoate (32.8 g, 0.2 mole), N-bromosuccinimide (40 g, 0.22 mole) and benzoyl peroxide (0.5 g) in carbon tetrachloride (200 ml) was heated under reflux for 75 minutes and then concentrated under vacuum. The residual mixture was partitioned between water (200 ml) and dichloromethane (200 ml). The organic layer was dried over MgSO4 and evaporated to give 52.6 g of light yellow oil. The oil was dissolved in hexane (200 ml), filtered, and dried over MgS04. The filtrate was concentrated under vacuum to give 49.2 g (100%) of crude product as a light yellow oil which was used in the next step without further purification. The $^1$H-NMR (300 MHz) spectral data was consistent with the desired product containing about 10% unreacted benzoate ester.

A mixture of sodium diatrizoate (25 g, 39 mmol) and crude ethyl 4-bromomethylbenzoate (12.2 g, 50 mmol) described above in 200 ml of DMF was stirred at room temperature for 6 hours and then concentrated to dryness under vacuum after standing overnight. The residue was slurried in 300 ml of water and the resulting insoluble solid was collected, washed with water and air dried. The crude product was digested with 300 ml of ethanol, collected and dried under vacuum at 100°–105° C. to give 27.6 g (91%) of analytically pure product, mp 234°–236° C. (dec.); CI-MS: MH+ 777. The $^1$H-NMR (300 MHz) spectral data was consistent with the desired product. Calculated for $C_{21}H_{19}I_3N_2O_6$: C 32.50, H 2.47, N 3.61; Found: C 32.73, H 2.35, N 3.41.

EXAMPLES 3-7

In a manner similar to Examples 1 and 2 above, the following compounds were synthesized: WIN 67956; WIN 67922; WIN 69738; WIN 69720 and WIN 68887. In each case, the $^1$H-NMR (300 MH$_z$) spectral data, CI-MS and the elemental analysis were consistent with the desired product.

EXAMPLE 8

Compound A was prepared in a manner similar to Example 1 except that benzylbromide was used in place of 4-methoxybenzyl chloride. The $^1$H-NMR and $^{13}$C-NMR were consistent with the desired product.

EXAMPLE 9

Compound A was deprotonated with 2.1 equivalents of sodium hydride in DMF and treated with 2.1 equivalents of 1-bromohexane to yield Compound B. The $^1$H-NMR, $^{13}$C-NMR and MH+ 873 were consistent with the desired product as an amide rotational isomer mixture.

The invention has been described in detail with particular reference to certain preferred embodiments thereof, but it will be understood that variations and modifications can be effected within the spirit and scope of the invention.

We claim:

1. A compound having the structure

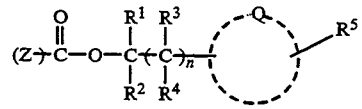

wherein (Z—COO is the residue of diatrizoic acid;
n is an integer from 0 to 6;
$R^1$ and $R^2$ are independently H, alkyl, fluoroalkyl, cycloalkyl, aryl, aralkyl, alkoxy or aryloxy;
$R^3$ and $R^4$ are independently H, alkyl, fluoroalkyl, cycloalkyl, aryl, aralkyl, alkoxy, aryloxy, halogen, hydroxy or acylamino;
Q represents the atoms necessary to complete a phenyl ring; and
$R^5$ is COO-alkyl.

2. The compound of claim 1 wherein $R^1=R^2=H$.

3. An x-ray contrast composition comprising the compound of claim 1.

4. The x-ray contrast composition of claim 3 further including a pharmaceutically acceptable carrier.

5. A compound having the structure

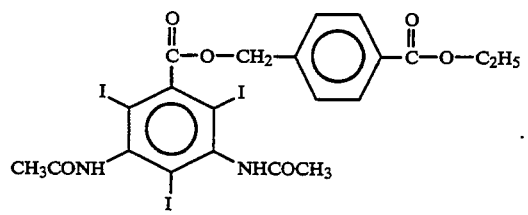

6. An x-ray contrast composition comprising the compound of claim 5.

7. The x-ray contrast composition of claim 6 further including a pharmaceutically acceptable carrier.

* * * * *